US006045831A

United States Patent [19]
Weitz et al.

[11] Patent Number: 6,045,831
[45] Date of Patent: Apr. 4, 2000

[54] NUCLEAR INHIBITOR I-92 AND ITS USE FOR THE PRODUCTION OF A MEDICAMENT

[75] Inventors: Jürgen Weitz, Durham, N.C.; Hans-Dieter Royer, Berlin-Buch, Germany; Michael Stöhr, Neckargerach, Germany; Marijana Kopun; Inge Napierski, both of Heidelberg, Germany

[73] Assignee: Dade Behring Marburg GmbH, Marburg, Germany

[21] Appl. No.: 08/183,909

[22] Filed: Jan. 19, 1994

Related U.S. Application Data

[63] Continuation of application No. 07/957,885, Oct. 7, 1992, abandoned.

[30] Foreign Application Priority Data

Oct. 9, 1991 [EP] European Pat. Off. ............... 91117184

[51] Int. Cl.[7] ..................................... A61K 35/12
[52] U.S. Cl. .......................... 424/520; 435/325; 435/366; 435/367; 436/501; 530/300; 530/350; 530/358; 530/412
[58] Field of Search .............................. 530/387.7, 387.1, 530/388.8, 388.85, 350, 358, 300, 413, 412; 424/520; 435/325, 366, 367; 436/501

[56] References Cited

PUBLICATIONS

Weitz, J., et al., "A Novel Nuclear Inhibitor I–92 Regulates DNA Binding Activity of Octamer Binding Protein p92 During the Cell Cycle," Nucleic Acids Res, vol. 19, No. 20, p. 5725–30, Oct. 25, 1991.

Delineation of Human Papillomavirus Type 18 Enhancer Binding Proteins: The Intracellular Distribution of a Novel Octamer Binding Protein p92 is Cell Cycle Regulated, Royer et al., Nucleic Acids Research, 19(9):2363–2371 (1991).

Characterization of a Cell Type–Specific Enhancer Found in The Human Papilloma Virus Type 18 Genome, Swift et al., The EMBO Journal, 6(5):1339–1344 (1987).

At Least Two Nuclear Proteins Bind Specifically to The Rous Sarcoma Virus Long Terminal Repeat Enhancer, Sealey et al., Molecular and Cellular Biology, 7(2)–787–798 (1987).

Transcriptional Regulation Of The Human Papillomavirus–16 E6–E7 Promoter By A Keratinocyte–Dependent Enhancer, And By Viral E2 Trans–Activator And Repressor Gene Products: Implications For Cervical Carcinogenesis, Cripe et al., The EMBO Journal, 6(12):3745–3753 (1987).

Human Papillomaviruses and Cervical Carcinoma, Vousden, Cancer Cells, 1(2):43–50 (1989).

In Situ Detection of Sequence–Specific DNA Binding Activity Specified By A Recombinant Bacteriophage, Vinson et al., Genes and Development, 2:801–806 (1988).

A Two–Base Change in a POU Factor–Binding Site Switches Pituitary–Specific to Lymphoid–Specific Gene Expression, Elsholtz et al., Genes & Development 4:43–51 (1990).

Transcriptional Activation of the human Papillomavirus–16 P97 Promoter by an 88–Nucleotide Enhancer Containing Distinct Cell–Dependent And AP–1 Responsive Modules, Cripe et al., The New Biologist, 2(5):450–463 (1990).

Expression of a Large Family of POU–Domain Regulatory Genes in Mammalian Brain Development, X. He et al., Nature, 340:35–42 (1989).

Cleavage of Structural Proteins During the Assembly of the Head of Bacteriophage T4, U.K. Laemmli, Nature, 227:680–685 (1970).

Correlation of Modified Human Papilloma Virus Early Gene Expression With Altered Growth Properties in C4–1 Cervical Carcinoma Cells, Doeberitz et al Cancer Research, 48:3780–3786 (1988).

Continued Expression of HPV–16 E7 Protein is Required for Maintenance of the Transformed Phenotype of Cells Co–Transformed by HPV–16 Plus EJ–ras, Crook et al., The EMBO Journal, 8(2):513–519 (1989).

The Retinoblastoma Susceptibility Gene Product Undergoes Cell Cycle–Dependent Dephosphorylation and Binding to and Release From SV40 Large T, Ludlow et al., Cell, 60:387–396 (1990).

Inducible and Constitutive Enhancer Domains in the Noncoding Region of Human Papillomavirus Type 18, Gius et al., Journal of Virology, 62(3):665–672 (1988).

IκB: A Specific Inhibitor of the NF–κB Transcription Factor, Baeuerle et al Science, 242:540–546 (1988).

Human Cell Hybrids: Analysis of Transformation and Tumorigenicity, Stanbridge et al., Science, 215:252–259 (1982).

Numerous Nuclear Proteins Bind the Long Control Region of Human Papillomavirus Type 16: A Subset of 6 of 23 DNase I–Protected Segments Coincides With the Location of the Cell–Type–Specific Enhancer, Gloss et al Journal of Virology, 63(3):1142–1152 (1989).

Interplay of Viral and Cellular Proteins Along the Long Control Region of Human Papillomavirus Type 18, Garcia–Carranca et al., Journal of Virology, 62(11):4321–4330 (1988).

Characterization of a Transcriptional Promoter of Human Papillomavirus 18 and Modulation of Its Expression by Simian Virus 40 and Adenovirus Early Antigens, Thierry et al., Journal of Virology, 61(1):134–142 (1987).

(List continued on next page.)

*Primary Examiner*—Ponnathapura Achutamurthy
*Assistant Examiner*—Nashaat T. Nasheed
*Attorney, Agent, or Firm*—Finnegan, Henderson, Farabow, Garrett & Dunner, L.L.P.

[57] ABSTRACT

The present invention concerns a nuclear inhibitor which specifically inhibits the activity of sequence specific DNA enhancer binding proteins of Human Papilloma Virus (HPV) and the use of this nuclear inhibitor for the production of a medicament for treatment of human cervical cancer.

6 Claims, 4 Drawing Sheets

OTHER PUBLICATIONS

Octamer Transcription Factors Bind to Two Different Sequence Motifs of the Immunoglobulin Heavy Chain Promoter, Kemler et al., The EMBO Journal, 8(7):2001–2008 (1989).

Eukaryotic Transcriptional Regulatory Proteins, Johnson et al., Annu. Rev. Biochem., 58:799–839 (1989).

Structure and Transcription of Human Papillomavirus Sequences in Cervical Carcinoma Cells, Schwarz et al., Nature, 314:111–114 (1985).

Clusters of Nuclear Factor 1 Binding Sites Identify Enhancers of Several Papillomaviruses But Alone Are Not Sufficient For Enhancer Function, Gloss et al., Nucleic Acids Research, 17(9):3519–3533 (1989).

Transcriptionial Activation of Human Papillomavirus 16 by Nuclear Factor 1, AP1, Steroid Receptors and a Possibly Novel Transcription factor, PVF: a Model for the Composition of Genital Papillomavirus Enhancers, Chong et al. Nucleic Acids Research, 18(3):465–470 (1990).

A Cloned Octamer Transcription Factor Stimulates Transcription From Lymphoid–specific Promoters in Non–B Cells, Müller et al., Nature, 336:544–551 (1988).

Transcription Factor AP–2 Mediates Induction By Two Different Transduction Pathways: Protein Kinase C and cAMP, Cell, 51:251–260 (1987).

DNA Binding Proteins Present in Guanidinium Isothiocyanate Lysates of Cells Are Suitable for Specific Binding Site Blotting, Nucleic Acids Research, 17(21):8891 (1989).

A Nuclear Factor That Binds to a Conserved Sequence Motif in Transcriptional Control Elements of Immunoglobulin Genes, Nature, 319:154–158 (1986).

Identification of a Novel Constitutive Enhancer Element and an Associated Binding Protein: Implications for Human Papillomavirus Type II Enhancer Regulation, Chin et al., Journal of Virology, 63(7):2967–2976 (1989).

A Novel Nuclear Inhibitor I–92 Regulates DNA Binding Activity of Octamer Binding Protein P92 During The Cell Cycle, J. Weitz et al., Nucleic Acids Acids Research, 19(20):5725–5730 (1991).

NUCLEAR INHIBITOR I-92 AND ITS USE FOR THE PRODUCTION OF A MEDICAMENT

This application is a continuation, of application Ser. No. 07/957.885, filed Oct. 7, 1992, now abandoned.

The invention relates to a compound which regulates the activity of a protein which binds to a DNA enhancer sequence of human papillomavirus.

Furthermore, the invention embraces the use of this compound for the production of a medicament for treating human cervical cancer and kits for the diagnosis of cervical tumors.

Cervical cancer represents the second most frequent cancer in females on a worldwide scale. DNA of human papillomaviruses with high oncogenic potential is found in over 90% of cervical cancer biopsies. Two proteins E6 and E7 with transforming activity are encoded by viral early genes and their continuous expression is required for maintenance of the proliferative and transformed phenotype (Cancer Res. 48, 3780–3786 (1988); EMBO J, 8, 513–519 (1989)). The transforming activities of E6 and E7 proteins are at least in part explained by the fact that they interact specifically with products of tumor suppressor genes $p105^{RB}$ and p53. $p105^{RB}$ is the product of the retinoblastoma susceptibility gene (Cell, 60, 387–396 (1990)). HPV18 early gene expression is under control of the upstream regulatory region (URR), which has three domains, where the most 5'region, adjacent to the L1 gene, is E6 responsive and the most 3'region, which contains the early gene promoter, is E2 responsive (J. Virol., 62, 665–672 (1988)). The enhancer of papillomavirus type 18 consists of two functionally redundant domains, one is partially conserved between HPV18 and HPV16, both mediate strong transcriptional enhancement. The enhancer is located on a 230 nucleotide long RsaI-RsaI fragment, and can be subdivided into two functionally redundant domains of similar size, whose activity depends on cellular transregulatory factors (EMBO J., 6, 1339–1344 (1987); J. Virol., 61, 134–142 (1987)). After infection of normal cells, viral DNA is episomal and in rare cases viral DNA integrates into the host genome. In the integrates early genes are expressed at low level. In contrast, in cervix cancer cells, viral DNA is usually integrated and the early genes E6 and E7 are invariably expressed at high level. In most cases, the viral genome uses for the integration event coding sequences of the E2 gene, which encodes the viral transregulatory protein E2 (Nature, 314, 111–114 (1985)). Upon integration in E2 coding sequences this protein is inactivated, and the early gene promoter is no longer E2 dependent. It is assumed that the early gene promoter is then predominantly controlled by host cell factors (Cancer Cells, 1, 43–50 (1989)). The understanding of mechanisms which regulate the expression of the transforming genes is of critical importance for the understanding of cervical carcinogenesis and, consequently, important for the production of effective medicaments against cervical cancer.

The enhancers of HPV16 and HPV18 contain recognition sites for nuclear factor I (NFI), activator protein AP1 and glucocorticoid receptors (Nucl.Acids.Res., 18, 465–470 (1990); EMBO J, 6, 3745–3753 (1987); New Biologist, 2, 450–463 (1990); J.Virol. 62, 4321–4330 (1988); Nucl. Acids.Res.17, 3519–3533 (1989). The activities of individual cis acting elements contribute to full enhancer activity. HPV enhancer function depends on the cooperative interaction of multiple factors, because short segments of the enhancer have only weak transactivating function, whereas the complete enhancer is a strong transactivator. Frequently recognition sites bind multiple proteins, and individual factors can interact with different recognition sequences (Genes Dev., 4, 43–51 (1990); Nature, 340, 3542 (1989); EMBO J. , 8, 2001–2008 (1989); Annu.Rev.Biochem., 58, 799–839 (1989)).

One of these nuclear factors is the protein p92 which binds at repeated sites in the enhancer (Nucleic Acids Research, Vol. 19, No. 9, 2363–2371, 1991). Recognition sequences for p92 were identified in a TTGCTTGCATAA sequence motif (SEQ ID NO.: 1). The p92 protein binds to enhancer oligonucleotides, containing at least one copy of Oct-1 like recognition sequences, these oligonucleotides also bind synthetic Oct-1 protein. Immunoblots of cytoplasmic extracts with anti-Oct-1 antisera showed, that p92 is an octamer binding factor, which is not immunologically related to the Oct-1 protein, and its intracellular distribution is regulated at the G0/G1 boundary of the cell cycle, by nucleo-cytoplasmic translocation.

It was found that the concentration of p92 is enhanced in some tumors and tumor cells. In contrast thereto, the DNA binding activity was not detected in normal non-transformed human fibro-blasts under the conditions of serum starvation. During serum starvation or at high saturation density, p92 moves from the nucleus into the cytoplasm and is no longer active because it is physically separated from its target sequences.

In various tumors, this regulation mechanism does not function. In cases where cells contain e.g. integrated HPV genomes and simultaneously produce increasing concentrations of p92, this may activate the enhancer. Consequently, this may lead to increased transcription of mRNAs which code for transforming proteins E6 and E7 which are involved in the transformation of human cells.

There is a need for effective therapeutic agents for the prevention, diagnosis and/or treatment of HPV related tumors.

It is a problem of the present invention to provide a factor which affects the regulation of HPV early gene expression in cervical carcinomas. It is a further problem to provide a medicament containing such a factor for the treatment of cervical carcinomas.

The solution of this problem is a nuclear inhibitor which specifically inhibits the activity of proteins which bind to DNA enhancer sequences of human papillomavirus.

A preferred embodiment of the invention is a compound referred to as nuclear inhibitor I-92 which inhibits specifically the activity of the human papillomavirus type 18 derived sequence specific DNA enhancer binding protein p92.

The compound I-92 was surprisingly found to prevent the nuclear protein p92 from binding to HPV DNA enhancer structures. The consequence of the activity of I-92 is the suppression of the expression of the HPV proteins E6 and E7 which are involved in the transformation of human cells.

The invention additionally embraces diagnostic kits for the identification of I-92 in cervical tissues with I-92 specific antibodies. The diagnostic kits contain polyclonal or monoclonal antibodies against the nuclear inhibitor which specifically inhibits the activity of proteins, which specifically bind to DNA enhancer sequences of human papillomavirus.

Cyclic association of a nuclear inhibitor with a sequence specific DNA binding protein is a novel principle of regulating cell cycle dependent activity of DNA binding. The inhibitor I-92 associates with p92 in G1 and G2 of the cell cycle, whereby DNA binding activity of p92 is inactivated. In S phase cells I-92 is not active, therefore p92 is not complexed, and can bind to the octamer sequences, which are present in the cellular genome and in HPV control regions. Active p92 can be released from the inactive complex by deoxycholate treatment. This observation suggests that the association of p92 with its inhibitor I-92 is reversible. In addition I-92 is able to reassociate with p92 in vitro to form an inactive complex. The formation of an inactive I-92:p92 complex with p92 from S phase cells in vitro, suggests that most likely the activity of the inhibitor is regulated by the cell cycle. If p92 itself would be regulated in its ability to associate with I-92, then p92 from S phase cells should not be inactivated by I-92 in vitro.

The cell cycle responds to extracellular signals, p92 is a mediator of extracellular signals, such as growth factor receptor response, which leads to the activation and nuclear import of p92. During transport p92 accumulates in the nucleus where its activity is controlled by the cell cycle. This type of regulation provides a mechanism whereby an extracellular signal leads to S phase dependent activity of a sequence specific DNA binding protein. The inhibitor I-92 behaves like a potential tumor suppressor protein.

Identification of Octamer Binding Protein p92 in Retarded Protein:DNA Complexes p92 is found in the cytosol of nontumorigenic Hela-fibroblast hybrid cells (Science 215, 252–259 (1982)), which are arrested at the G0/G1 boundary of the cell cycle. Culture conditions, which lead to cell cycle arrest, are growth to high saturation density or serum starvation. The octamer binding protein p92 was identified by binding site blotting, with a synthetic double stranded oligonucleotide, which was derived from the human papillomavirus type 18 enhancer, and contained two octamer related sequences (Nucleic Acid Research Vol. 19, No. 9, 2363–2371 (1991)). The assignment of proteins, which have been identified by binding site blotting, to retarded DNA complexes in Electrophoretic mobility shift analysis (EMSA) is not easily achieved, because the charge of proteins will affect their mobility in a native gel. Therefore, a correlation between the molecular weight of a given protein with the extent of retardation in EMSA is not possible.

EMSA was used to detect p92 DNA binding activity, because of its greater sensitivity. To identify retarded DNA-protein complexes containing p92 protein, preparative EMSA in combination with binding site blotting was used. For preparative EMSA oligo-nucleotide RP3 was used, which contains p92 binding sites, and cytosol from nontumorigenic Hela-fibroblast hybrid cells at high saturation density. In analytical EMSA new retarded DNA-protein complexes appear at high saturation density. Applicant has isolated proteins which are present in retarded complex A and in retarded complex B by preparative EMSA. After autoradiography retarded complexes were eluted, and proteins were precipitated with 9 volumes of acetone in the presence of 20 µg BSA at 4° C. over night. Proteins were analyzed by binding site blotting with oligonucleotide RP3 as a probe. The retarded DNA-protein complexes both contain p92. This experiment demonstrates that p92 is contained in retarded complex A and complex B. The carrier protein bovine serum albumin did not contain any DNA binding activities. It is not known whether in complex B p92 is bound as a dimer, or whether p92 interacts with a second protein.

Cytosolic p92 protein binds to octamer related sequences derived from the human papillomavirus enhancer. The cytosolic p92 also binds with high affinity to a highly conserved octamer sequence of the immunoglobulin heavy-chain promoter (Nature, 336, 544–551 (1988)). The octamer consensus sequence, which is present in the heavy-chain promoter is 27 nucleotides long, and contains an additional heptamer sequence. For binding site blotting this 27 nucleotide long sequence was synthesized as a dimer. This oligo-nucleotide represents a specific Oct-1 binding site, which is part of the gene control region of a cellular gene. Cytoplasmic p92, which is present in the cytosol of various cancer cell lines in high density cells, binds with high affinity to this oligonucleotide in a binding site blot. This result shows that p92 binds to the consensus octamer sequence, and demonstrates that p92 is an octamer binding protein.

DNA Binding Activity and Nuclear Import of Octamer Binding Protein 92 are Regulated by Extracellular Signals In contact inhibited, quiescent fibroblasts, p92 DNA binding activity could not be detected in the nucleus or cytosol. In serum starved fibroblasts (40 hrs, in medium containing 0.5% FCS) retarded p92-DNA complexes cannot be detected in EMSA of the cytoplasmic fraction. After the addition of fresh medium containing 10% fetal calf serum, p92 DNA binding activity appears within 3 hours in the cytosol, with maximal concentration after 5 hours. 9 hours after serum stimulation p92 starts to disappear from the cytosol, and most p92 has disappeared after 12 hours. Nuclear transport of p92 starts 7 hours after serum stimulation and nuclear import is completed after 12 hours. In serum starved fibroblasts, p92 DNA binding is induced by serum stimulation within three hours.

In nontumorigenic Hela-Fibroblast hybrid cells (444), p92 DNA binding activity is found in the cytosol, at high saturation density. In serum starved cells p92 is also cytoplasmic and p92 DNA binding activity remains detectable even 40 hours after cells were transferred into medium containing 0.5% fetal calf serum. After the addition of medium containing 10% FCS, the retarded p92:DNA complex does not detectably change. Five hours after growth in high serum (10% fetal calf serum), a novel retarded complex appears in the cytosol, which may be related to complex B, which contains p92 and a possible p92 dimer. Subsequently the p92 concentration ceases, and after 9 hours p92 is no longer detectable in the cytosol. In nuclear extracts of 444 cells, after serum starvation only traces of p92 are present. After serum stimulation, nuclear import of p92 begins within 5 hours, and is maximal after 9 hours, this is the time point where all cytosolic p92 has disappeared. The regulation of p92 nuclear import requires additional signals, because the presence of active DNA binding p92 in the cytosol of serum starved 444 cells does not lead to nuclear translocation. The intracellular distribution of p92 is therefore tightly regulated by extra-cellular signals, such as growth factors which are present in serum (EGF, PDGF).

DNA Binding Activity of Nuclear p92 is Cell Cycle Regulated

Extracellular signals regulate DNA binding activity and nuclear import of p92. The kinetics of nuclear import are slow and p92 appears in the nucleus twelve hours after the addition of serum to serum starved fibroblasts. This kinetic suggests that p92 appears in the nucleus before the beginning of S phase. In nuclear extracts of asynchronously growing cells, which have not yet reached confluence, p92 is found in the nucleus but not in the cytoplasm. To study the fate and activity of nuclear p92 during the cell cycle, asynchronous populations of nontumorigenic Hela-fibroblast hybrid cells (444) and fibroblasts were separated by centrifugal elutriation into fractions of G1-, S-, and G2-phase cells. The first fraction and the last fraction contained 82% G1 cells and 85% G2 cells respectively. From these separated cell populations nuclear extracts were analyzed by EMSA for p92 DNA binding activity. In EMSA of nuclear extracts from nontumorigenic Hela-fibroblast hybrid cells, p92 DNA binding activity is only present in S phase. Two retarded complexes A and B can be detected in S phase nuclear extracts of 444 cells, these complexes may both contain p92. Similar retarded complexes were analyzed by preparative EMSA and binding site blotting, and both contained p92. After nuclear import, p92 DNA binding activity persists in S phase and is abolished in G2. In G1 cells p92 is not active and it seems that p92 is activated in S phase cells.

I-92 Regulates S Phase Dependent p92 DNA Binding Activity

Nuclear and cytoplasmic fractions of nontumorigenic Hela-fibro-blast hybrids, which were separated by centrifugal elutriation into G1-, S-, and G2-cells were analyzed by binding site blotting.

The oligonucleotide RP3, which was used in EMSA, was used as a probe. The binding site blot (FIG. 1) shows, that p92 is present in nuclei of early S- and late S-phase cells of the cell cycle (lanes 3 and 4), in G1 and G2, however, equal amounts of p92 are present as well (lanes 2 and 5). No p92 is found in the cytosol of G1, S or G2 cells (lanes 6, 7, 8, 9). This shows that in cells, which grow asynchronously in culture, p92 is located in the nucleus. The DNA binding activity of nuclear p92 is not only present in S phase cells but is also present in G1- and G2-cells. This is in contrast to results which were obtained by EMSA of G1-, S- and G2-cells. This observation rules out that the p92 DNA binding activity itself is regulated by the cell cycle. One possibility to explain this cell cycle regulation of DNA binding activity is the existence of a nuclear inhibitor of p92, which is only active in G1and G2 of the cell cycle. The association of p92 with the putative inhibitor in G1- and G2-cells can be detected by EMSA, but not by a denaturing procedure like binding site blotting.

The inventors have used the method in Science 242, 540–546 (1988) to determine, whether in G1-, and G2-cells an inactive p92 complex exists. For EMSA oligonucleotide RP3 was used and nuclear extract from 444 cells which were separated by centrifugal elutriation into fractions of G1- and G2-cells. The addition of 0.2% sodium deoxycholate (DOC) into the binding reaction of G1 nuclear extract, leads to the appearance of a novel retarded complex, which is retarded to a similar extent as p92:DNA complex A in S phase cells (FIG. 2 panel A, lanes 2 and 3). This shows that p92 is complexed in crude extracts of G1 cells to an inhibitor of DNA binding. DOC treatment of G2 nuclear extract releases a similar retarded complex (FIG. 2 panel B, lane 2). This demonstrates that in nuclear extracts of 444 cells, which are in G1 and G2 of the cell cycle, p92 DNA binding activity is complexed to a nuclear inhibitor of p92 DNA binding. The activity of this inhibitor is regulated by the cell cycle. The nuclear inhibitor is called I-92. The mechanism which regulates S phase activity is the cyclic association of p92 with its inhibitor I-92 in G1 and G2 of the cell cycle. The association of p92 with I-92 is reversible, because active p92 can be released from the inactive complex by DOC treatment.

In human fibroblasts p92 DNA binding is also restricted to S phase cells. Human fibroblasts were separated into G1-, S- and G2-cells and nuclear extracts were analyzed by EMSA. The separation into highly enriched G1, S and G2 populations is not as good, because fibroblasts have the tendency to be more adherent than the Hela-fibroblast cells. The activity of p92 is predominantly confined to S phase (FIG. 3A, lane 2). In this preparation, however low p92 activity was observed in G1cell extracts, this may be the result of prolonged trypsinization, because of contaminating G2 cell nuclei in the G1 fraction. In contrast no p92 DNA binding activity is found in G2 fibroblast nuclear extracts. In G2 fibroblast nuclear extract p92 is complexed to a DOC sensitive complex with the inhibitor I-92 (FIG. 3b, lanes 2 and 3). This shows the existence of the inhibitor I-92 in normal human cells, and also shows that the cell cycle regulation of p92 DNA binding by cyclic association of p92 with its inhibitor I-92 is operating in these normal human fibroblasts.

The Inhibitor I-92 Associates In Vitro with p92 and Inactivates its DNA Binding Activity I-92 has no DNA binding activity. In order to test this, nuclear extracts of nontumorigenic Hela-fibroblast hybrids (444) were treated with 0.2% DOC, and subsequently passed over a heparin SPHAROSE column in 70 mM NaCl. The flow through was collected. After washing the column in loading buffer, bound proteins were eluted with 600 mM NaCl. In EMSA, the flow through did not induce any retarded DNA-protein complexes, and the 600 mM eluate contained all p92 binding activity. In EMSA from S phase cells, which contain no detectable I-92 activity, there are three retarded complexes formed. The top two complexes correspond to p92:DNA complex A and B (FIG. 4, lane 1). The identity of the protein in complex C is currently under investigation. For the identification of I-92 in the heparin SEPHAROSE flow through, increasing amounts of flow through are added to the DNA binding reaction of S phase nuclear extract and the oligonucleotide RP3, which contains a p92 recognition site. The addition of 5 $\mu$l flow through reduces strongly complex B and to some extent complex A (FIG. 4, lane 2). The addition of 15 $\mu$l flow through prevents completely the formation of complex B, after addition of 20 $\mu$l of flow through neither complex B nor complex A is formed. The formation of complex C is unaffected by the addition of flow through to the DNA binding reaction. The persistence of complex C after the addition of 20 $\mu$l flow through to the reaction shows that I-92 associates specifically with p92 in vitro whereby its DNA binding activity is inactivated.

DESCRIPTION OF THE FIGURES

FIG. 3A EMSA of nuclear extracts of human fibroblast nuclear extracts, which were separated into G1 , S, and G2 cells by centrifugal elutriation. G1 cells (lane 1), early S phase cells (lane 2), late S phase cells (lane 3) and G2 cells (lane 4). The position of a p92 retarded complex is indicated.

FIG. 3B EMSA of fibroblast nuclear extract from G2 cells (lane 1), after treatment with 0.2% DOC (lane 2) and 0.4% DOC (lane 3).

EXAMPLE 1

Cell Culture and Cell Lines

Figure 1:
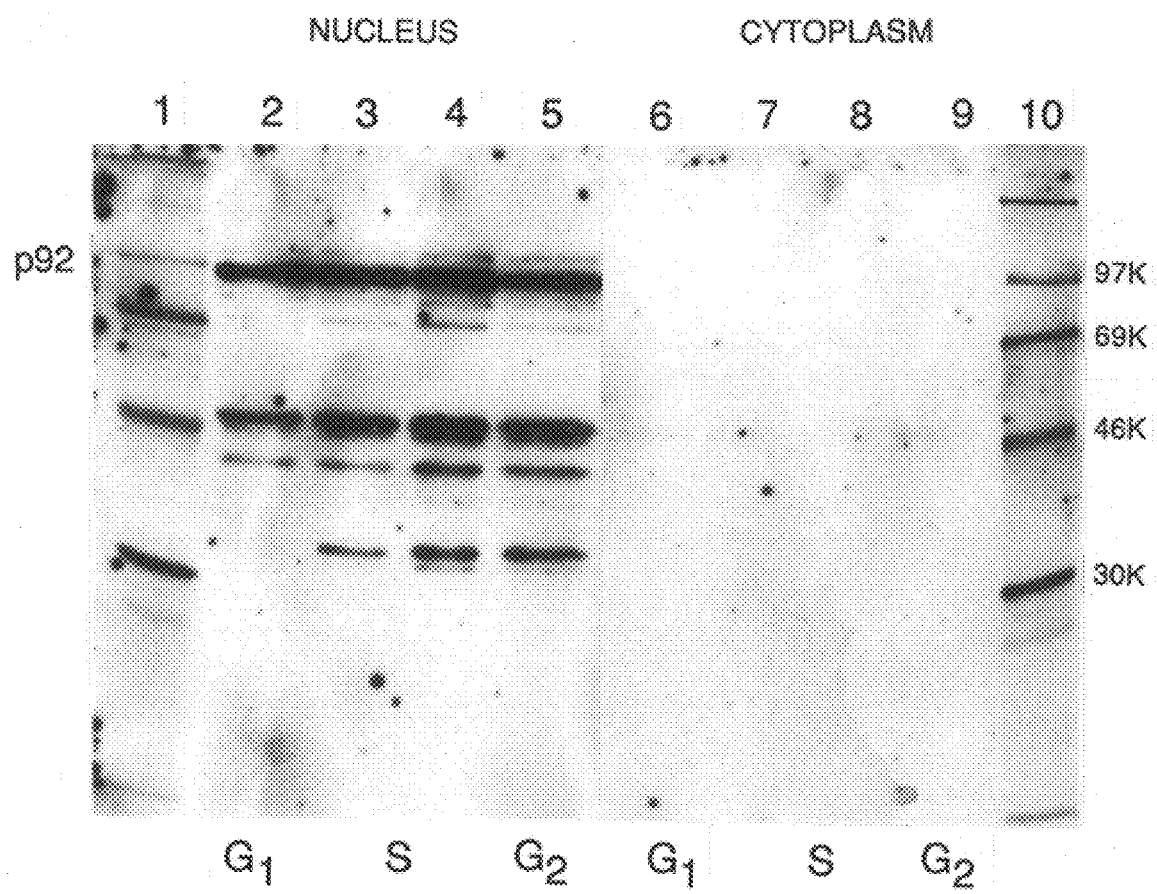
FIG. 1 Binding site blotting reveals p92 DNA binding activity throughout the cell cycle Binding site blot of nuclear and cytoplasmic 444 extracts from G1, S phase and G2 of the cell cycle, showing that p92 DNA binding activity is present in all phases of the cell cycle. p92 DNA binding activity in nuclear extracts of cells in G1 (lane 2), in early S phase (lane 3), in late S phase (lane 4) and in G2 (lane 5). Cytoplasmic extracts from cells in G1 (lane 6), in early S phase (lane 7), in late S phase (lane 8) and in G2 (lane 9).
Figure 2:
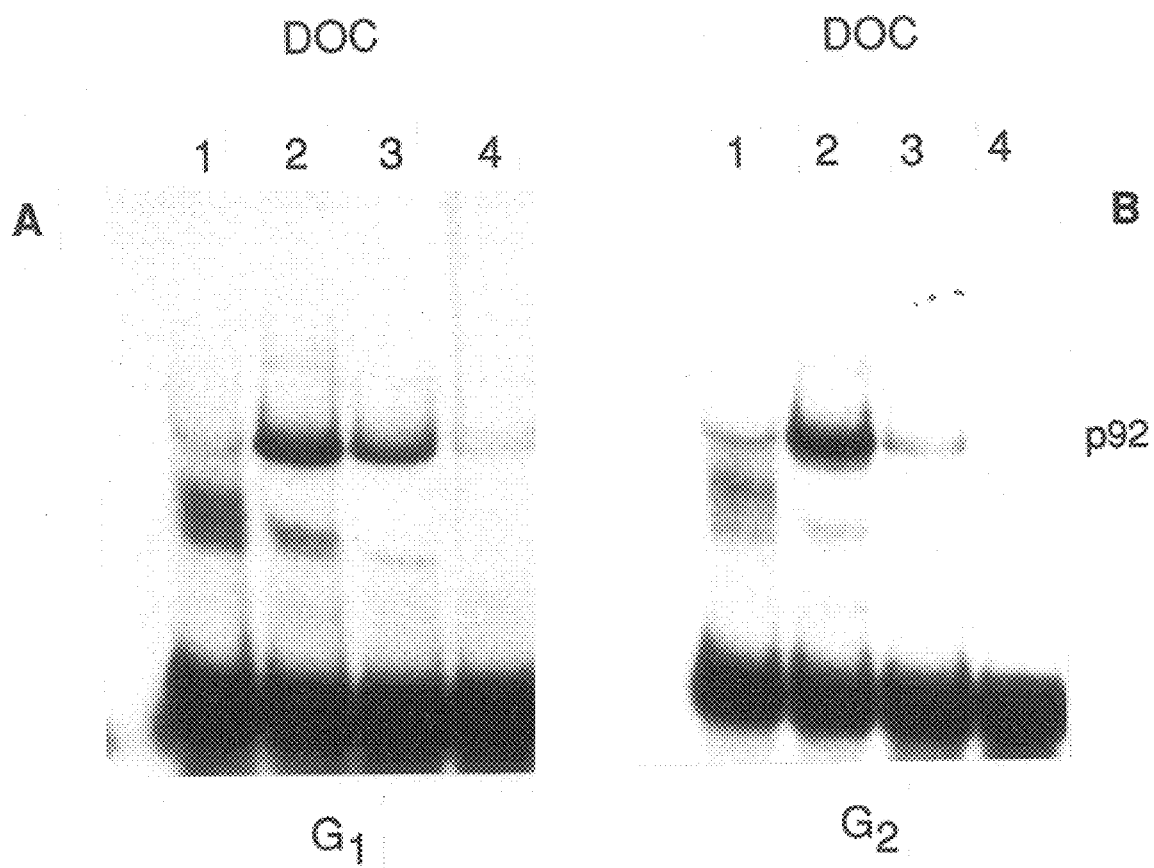
FIG. 2 I-92, a novel nuclear inhibitor of p92 regulates S phase dependent p92 DNA binding activity (A) EMSA of nuclear extracts from 444 cells in G1 (lane 1) shows that p92 DNA binding activity can be released by sodium deoxycholate treatment. 0.2% DOC (lane 2), 0.4% DOC (lane 3) and 0.6% DOC (lane 4). (B) EMSA of nuclear extracts. p92 DNA binding activity of cells in G2 (lane 1) can be induced by 0.2% DOC treatment (lane 2), nuclear extract after treatment with 0.4% DOC (lane 3) and after treatment with 0.6% DOC. Oligonucleotide RP3 was used for EMSA.
Figures 3A, 3B:
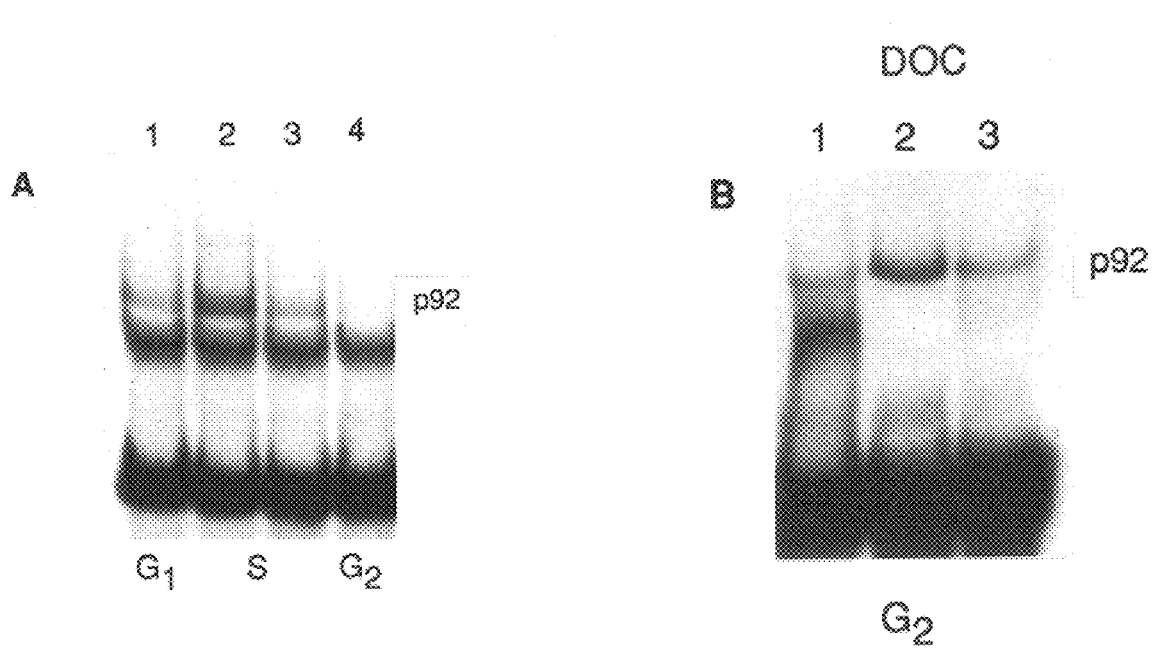
FIGS. 3A and 3B The inhibitor I-92 regulates S phase dependent DNA binding activity of p92 during the cell cycle in normal human fibroblasts.
Figure 4:
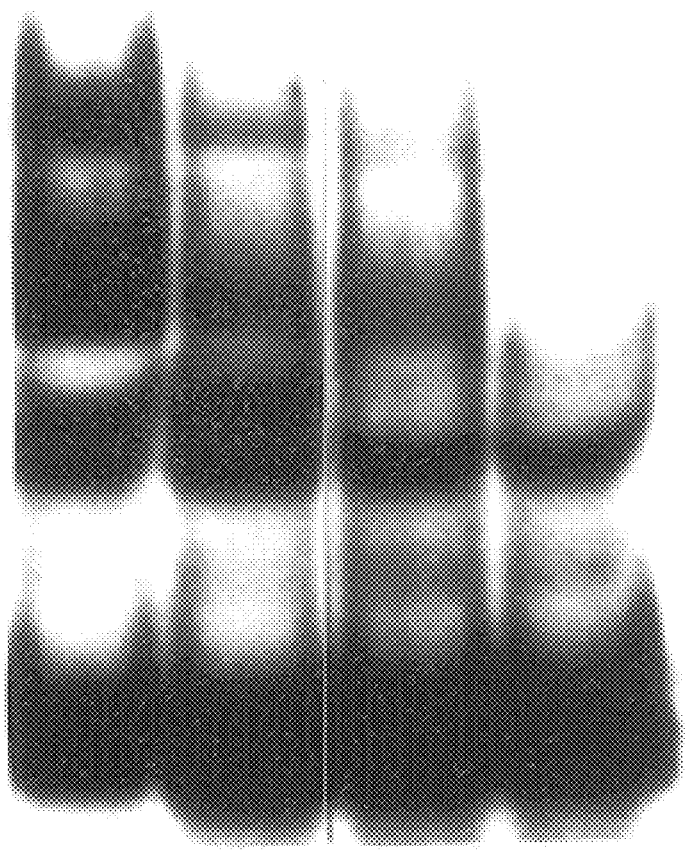
FIG. 4. The inhibitor I-92 associates with p92 in vitro and inhibits p92 DNA binding Nuclear extracts from confluent 444 cells were treated with 0.2% DOC and passed over a heparin SEPHAROSE column. The flow through was used as a source of I-92. EMSA of nuclear extract from 444 cells in S phase, where I-92 is inactive (lane 1), after the addition of 5 μl heparin SEPHAROSE flow through (lane 2), after the addition of 10 μl flow through (lane 3) and after the addition of 20 μl flow through (lane 4).

Hela-fibroblast hybrid cell lines (Science 215, 252–259 (1982)), and normal human fibroblasts were maintained in Dulbecco's Modified Eagle's Medium (DMEM) supplemented with 10% fetal calf serum. Hela-fibroblast hybrid cell lines were provided by Dr. Stanbridge, and human fibroblasts were provided by colleagues of the DKFZ. For serum starvation experiments, cells were grown subconfluent in DMEM containing 10% fetal calf serum, subsequently cells were held in DMEM containing 0.5% fetal calf serum for 40 hr. In serum stimulation experiments, cells were first serum starved for 40 hr and subsequently cells were grown in DMEM containing 10% fetal calf serum. For growth to high saturation density, cells at confluence were held in DMEM containing 10% fetal calf serum for 48 hr.

EXAMPLE 2

Extraction of Nuclear and Cytoplasmic Proteins

Nuclear extracts of cervical cancer derived cell lines and human fibroblasts were prepared according to a published procedure (Mol. Cell. Biol., 7, 787–798 (1987)). After detergent lysis with 0.65% NP-40 nuclei are prepared by low speed centrifugation at 4° C. and proteins eluted with 520 mM NaCl with slight agitation. For storage the eluates were dialyzed against a buffer containing 50% glycerol, 50 mM NaCl, 10 mM Hepes (pH 7.9), 0.5 mM PMSF and 0.5 mM DTT. Protein concentrations were determined by a colorimetric assay (Biorad) using serum albumin as a standard. Nuclear proteins from Hela cells and a B lymphoblastoid line (Laz 509) were enriched by heparin SEPHAROSE chromatography as described (Nature, 317, 84–87 (1985)). Cytoplasmic proteins were prepared after cell lysis and removal of nuclei by low speed centrifugation. Cytoplasmic proteins were dialyzed as described above for nuclear proteins.

EXAMPLE 3

Synthetic Oligonucleotides

Single stranded oligonucleotides and the complementary strands were synthesized on Applied Biosystems DNA synthesizers and purified by preparative denaturing acrylamide gel electrophoresis (Molecular Cloning: A Laboratory Manual (Cold Spring Harbor Laboratory, Cold Spring Harbor, N.Y.) (1982)). Full length bands were identified by UV shadowing, excised, eluted by diffusion in 500 mM ammonium acetate and ethanol precipitated. To generate double stranded oligonucleotides complementary strands were annealed at temperatures minus 3° C. below the specific melting points (Tm). Radiolabeled double stranded oligonucleotides were prepared with polynucleotide kinase and 32P-gamma ATP. The sequence for the recognition site of AP2 was from the human metallothionein IIA (hMT-IIA) gene control region (Cell, 51, 251–260 (1987)). The human papillomavirus enhancer sequence (J. Virol. 61, 134–142 (1987)) was used for synthesizing enhancer oligonucleotides RP2, RP3, RP3/4, RP4, RP5, S1tet and S2tet.

EXAMPLE 4

Binding Site Blotting

Nuclear proteins were size fractionated on 8% SDS polyacrylamide gels (Nature, 329, 680–685 (1970)) and transferred to nitrocellulose at 150 mA overnight at room temperature with a horizontal blotting chamber (IBI) in Laemmli running buffer without SDS. After blotting bound proteins were denatured in situ by 6M guanidinium hydrochloride and renatured by sequential dilution of guanidinium as described (Nucl.Acids.Res., 17:8891 (1989); Genes Dev., 2, 801–806 (1988)). Nitrocellulose membranes were blocked with 5% nonfat dry milk (Carnation) for 30 min at room temperature and subsequently incubated with end labeled double stranded oligonucleotides at $5 \times 10^5$ cpm/ml in the presence of 5 μg/ml poly(dIdC)(dIdC) as nonspecific competitor. The buffers for DNA binding and conditions for washing binding site blots were as described (Nucl.Acids.Res. 17:8891 (1989)).

EXAMPLE 5

Electrophoretic Mobility Shift Analysis (EMSA)

EMSA was carried out as described (Nature, 319, 154–158 (1986)). For EMSA of enhancer domain I, functional domain I of the HPV18 enhancer was isolated from pURR 18, a clone containing the up-stream regulatory region of HPV18, which is located on a 1050 bp BamHI fragment. In this fragment the enhancer is present on a RsaI-RsaI fragment (NT 582–810). This fragment was isolated by polyacrylamide gel electrophoresis and electroelution after RsaI and Fnu4H I digestion. The digestion with Fnu4H I (position 910) removes a comigrating promoter fragment. For EMSA of one functional domain, which is located on a BstNi-RsaI fragment (nucleotides 697–810), the RsaI(582)–RsaI(810) fragment was digested with BstNI and radiolabeled with polynucleotide kinase. The fragment containing enhancer domain I was isolated by polyacrylamide gel electrophoresis and electroelution. The incubations of enhancer domain I with nuclear protein contained 5 μg nuclear extract and 2.5 μg poly(dIdC)(dIdC) as nonspecific competitor. For EMSA DNA's were incubated in binding buffer (Nature, 319, 154–158 (1986)), for 25 min at room temperature and loaded on a low salt polyacrylamide gel (4% total monomer, 30:1 acrylamide/N,N'-methylenebisacrylamide ratio). Electrophoresis was at 11 V/cm for 90 min at room temperature. Gels were dried and exposed to X-ray film overnight.

EXAMPLE 6

Preparative EMSA

For preparative EMSA 24 individual samples corresponding to 120 μg nuclear extract were electrophoresed as for analytical EMSA. After autoradiography of the polyacrylamide gel at 4° C. over night, retarded complexes were excised and eluted from the gel in elution buffer:50 mM Tris HCl (pH 7.9), 0.1% SDS, 0.1 mg/ml bovine serum albumin, 1 mM DTT, 0.2 mM EDTA, 0.1 mM PMSF, 2.5% glycerol, for 12 hr at 4° C. Proteins from retarded complexes were precipitated with 9 volumes of acetone at −20° C. over night and recovered by centrifugation at 13000 rpm. For binding site blotting pelleted proteins were solubilized in SDS-PAGE loading buffer.

EXAMPLE 7

Sodium Deoxycholate Treatment of Nuclear Extracts and Heparin Sepharose Chromatography Nuclear extract from 444 cells (1 mg) was treated with 0.4% sodium deoxycholate (DOC) for 15 min at room temperature in 2 ml of. DNA binding buffer:25 mM Hepes (pH 7.9), 50 mM NaCl, 10% glycerol, 0.05% NP-40, 1 mM DTT, 1 mM EDTA. Before loading the DOC treated nuclear extract on a heparin SEPHAROSE column, DOC was complexed by the addition of 1.2% NP-40. After loading the column the flow through was passed over the column once more. The final flow through (2 ml) was used as a source for the inhibitor. Bound proteins were eluted from the heparin SEPHAROSE column after a G50 washing step, with G600 buffer, containing 600 mM NaCl. Besides NaCl, G50 and G600 buffers contained 10 mM Tris HCL (ph 7.5), 50 mM NaCl, 1 mM EDTA, 1 mM DTT, 5% glycerol, 0.2% DOC, 0.2% NP-40, 0.5% PMSF. The procedure followed published protocols (Science, 242, 540–546 (1988)).

EXAMPLE 8
Detection of Inhibiting I-92 Activity

Nuclear extracts from S phase 444 cells (5 μg) were incubated with increasing amounts of DOC treated 444 extract which was passed over a heparin SEPHAROSE column. The inhibiting I-92 activity was from the heparin SEPHAROSE flow through fraction.

EXAMPLE 9
Separation of Cells by Elutriation

Cell monolayers which were no more than 80% confluent were harvested with trypsin, resuspended in medium containing serum and elutriated. For the elutriation, $10^7$–$10^8$ cells were introduced into the JE-6B Beckman elutriation rotor connected with the Masterflex pump head. The elutriation was performed in Earle's balanced salt solution pH 7.4 buffered with 10 mM Hepes. Human embryonic lung fibroblasts were elutriated at 2000 rpm. The loading flow rate was 14 ml/min, the fractions used in this study were collected at 15–20 ml/min, 26–28 ml/min, 35–38 ml/min, and 47–50 ml/min. The nontumorigenic Hela-fibroblast hybrid (444) cells were elutriated at 1620 rpm after loading the cells at 5 ml/min. The flow rates for obtaining the fractions were 8–11 ml/min, 15–18 ml/min, 24–30 ml/min, and 34–38 ml/min. Samples of each fraction were ethanol fixed, dapi (4,6-di-amidino -2-phenyl indole) stained, and analyzed for the relative DNA content by means of a fluorescence activated cell sorter.

(c) is found in the nucleus of nontumorigenic Hela-fibroblast hybrid cells or normal human fibroblasts, and (d) has its in vivo activity regulated by said cell cycle.

2. A method of making a partially purified nuclear inhibitor as claimed in claim 1 which comprises:

(a) preparing a sodium deoxycholate treated nuclear extract from nontumorigenic Hela-fibroblast or normal human fibroblast cells, (b) loading that nuclear extract on a heparin agarose column, and (c) using the flow through as a source of said inhibitor.

3. A method for treatment of human cervical cancer which comprises suppressing expression of HPV proteins E6 and E7 with an inhibitor as claimed in claim 1.

4. A method of detecting the inhibiting activity of an inhibitor as claimed in claim 1, said method comprising:

(a) combining a sample containing said inhibitor with a sample containing p92 and a sample containing all oligonucleotide containing at least one copy of a p92 recognition sequence, and (b) detecting inhibition of binding of said p92 to said oligonucleotide.

5. The method of claim 4, wherein said oligonucleotide is labeled.

6. A partially purified nuclear inhibitor I-92, prepared by a process comprising the steps of:

(a) preparing a sodium deoxycholate treated nuclear extract from nontumorigenic Hela-fibroblast or normal human fibroblast cells,

---

---

We claim:

1. A partially purified nuclear inhibitor I-92, wherein said inhibitor (a) binds reversibly to the DNA binding protein p92 in G1 and G2 of the cell cycle, thereby forming an inactive sodium deoxycholate sensitive complex, (b) specifically inhibits the binding activity of p92 to DNA enhancer sequences of Human Papillomavirus, (b) loading that nuclear extract on a heparin agarose column, and (c) using the flow through as a source of said inhibitor wherein said inhibitor specifically inhibits p92 DNA binding activity in vitro.

\* \* \* \* \*

UNITED STATES PATENT AND TRADEMARK OFFICE
CERTIFICATE OF CORRECTION

PATENT NO. : 6,045,831
DATED : April 04, 2000
INVENTOR(S) : Jürgen Weitz et al.

It is certified that error appears in the above-identified patent and that said Letters Patent is hereby corrected as shown below:

Claim 4, Column 10, Line 18, "containing all" should read --containing an--.

Signed and Sealed this

Twenty-seventh Day of February, 2001

Attest:

NICHOLAS P. GODICI

Attesting Officer        Acting Director of the United States Patent and Trademark Office

SEQUENCE LISTING

<160> NUMBER OF SEQ ID NOS: 1

<210> SEQ ID NO 1
<211> LENGTH: 12
<212> TYPE: DNA
<213> ORGANISM: Human papillomavirus type 18

<400> SEQUENCE: 1
ttgcttgcat aa                                                          12